(12) United States Patent
Vivien et al.

(10) Patent No.: US 11,654,230 B2
(45) Date of Patent: May 23, 2023

(54) PLATE FOR HOLDING DRUG INJECTION DEVICE TUBES

(71) Applicant: CROSSJECT, Dijon (FR)

(72) Inventors: Gilles Vivien, Malakof (FR); Xavier Vigot, Veronnes (FR); Magalie Labrot, Amange (FR)

(73) Assignee: CROSSJECT, Dijon (FR)

( * ) Notice: Subject to any disclaimer, the term of this patent is extended or adjusted under 35 U.S.C. 154(b) by 0 days.

(21) Appl. No.: 16/707,729

(22) Filed: Dec. 9, 2019

(65) Prior Publication Data

US 2020/0114063 A1 Apr. 16, 2020

Related U.S. Application Data

(63) Continuation of application No. PCT/FR2018/051343, filed on Jun. 8, 2018.

(51) Int. Cl.
*A61M 5/00* (2006.01)
*B65D 25/10* (2006.01)

(52) U.S. Cl.
CPC ........... *A61M 5/001* (2013.01); *B65D 25/108* (2013.01)

(58) Field of Classification Search
CPC ...... B65D 25/108; B65D 25/10; A61M 5/001; A61M 5/002; A61M 5/008
USPC ........................................................ 206/364
See application file for complete search history.

(56) References Cited

U.S. PATENT DOCUMENTS

| | | | | |
|---|---|---|---|---|
| 832,086 A * | 10/1906 | Schweitzer | ............. | A47F 5/112 211/73 |
| 2,964,348 A * | 12/1960 | Ingham | .................. | B65D 71/50 294/87.28 |
| 3,144,269 A * | 8/1964 | Orr | ......................... | B65D 71/50 294/87.28 |
| 3,285,410 A * | 11/1966 | Brunsing | ............... | B65D 71/50 206/199 |
| 4,184,592 A * | 1/1980 | Howard, Jr. | ........... | B65D 71/70 206/327 |
| 5,080,232 A * | 1/1992 | Leoncavallo | ............. | B01L 9/06 206/443 |
| 5,396,989 A * | 3/1995 | Hein | ..................... | A61B 17/205 206/366 |
| 5,443,298 A * | 8/1995 | Finley | ..................... | B65D 71/50 206/148 |

(Continued)

FOREIGN PATENT DOCUMENTS

| | | |
|---|---|---|
| FR | 3038232 | 1/2017 |
| JP | 3026990 | 7/1996 |

(Continued)

OTHER PUBLICATIONS

International Search Report for International Application PCT/FR2018/051343, dated Sep. 3, 2018.

*Primary Examiner* — Steven A. Reynolds
(74) *Attorney, Agent, or Firm* — Burris Law, PLLC

(57) ABSTRACT

A tray intended to hold injection device tubes includes a collar at each end of a body. In order to carry out operations of preparing the injection device tubes, the tray includes bores and each bore is configured to receive a body of an injection device tube. Also, each bore of the tray includes a holding portion for holding the upper collar of the tube and the holding portion extends laterally from an introduction portion enabling the passage of the lower collar.

7 Claims, 2 Drawing Sheets

(56) References Cited

U.S. PATENT DOCUMENTS

| | | | | |
|---|---|---|---|---|
| 5,452,810 | A * | 9/1995 | Schwartz | B01L 9/06 |
| | | | | 206/446 |
| 6,394,329 | B1 * | 5/2002 | Magee | A45F 5/02 |
| | | | | 224/249 |
| 6,796,440 | B2 * | 9/2004 | Wang | A47F 7/0028 |
| | | | | 211/183 |
| 6,997,362 | B1 * | 2/2006 | Pidcock | A45B 1/04 |
| | | | | 135/66 |
| 7,910,067 | B2 * | 3/2011 | Knight | G01N 35/025 |
| | | | | 422/562 |
| 8,505,723 | B2 * | 8/2013 | Clark | B65D 5/503 |
| | | | | 206/443 |
| 8,561,828 | B2 * | 10/2013 | Krauss | A61J 1/16 |
| | | | | 220/507 |
| 10,124,928 | B2 * | 11/2018 | Wissner | B65B 7/2892 |
| 10,717,177 | B2 * | 7/2020 | Dembeck | B25B 23/005 |
| 2007/0026171 | A1 * | 2/2007 | Extrand | B65D 1/36 |
| | | | | 428/34.1 |
| 2007/0151882 | A1 * | 7/2007 | Cocheteux | A61M 5/008 |
| | | | | 206/366 |
| 2014/0034545 | A1 * | 2/2014 | Pawlowski | B65B 3/003 |
| | | | | 206/565 |
| 2015/0122693 | A1 * | 5/2015 | Deutschle | B65D 1/36 |
| | | | | 206/562 |
| 2016/0130022 | A1 * | 5/2016 | Wissner | B65B 43/42 |
| | | | | 53/486 |
| 2017/0100543 | A1 | 4/2017 | Cabiri et al. | |

FOREIGN PATENT DOCUMENTS

| | | |
|---|---|---|
| JP | 2003040253 | 2/2003 |
| JP | 2005313923 | 11/2005 |

* cited by examiner

PLATE FOR HOLDING DRUG INJECTION DEVICE TUBES

CROSS-REFERENCE TO RELATED APPLICATIONS

This application is a continuation of International Application No. PCT/FR2018/051343, filed on Jun. 8, 2018, which claims priority to and the benefit of FR 17/55198, filed on Jun. 9, 2017. The disclosures of the above applications are incorporated herein by reference.

FIELD

The present disclosure relates to a tray for holding drug injection device tubes, as well as methods for processing tubes implementing such a holding tray.

BACKGROUND

The statements in this section merely provide background information related to the present disclosure and may not constitute prior art.

One known type of injection device, presented in particular by the document FR-A1-3038232, carries out intradermal, subcutaneous or intramuscular needleless injections of active ingredients contained in a fluid for therapeutic use in human medicine or in veterinary medicine. The fluid may be a gel or a more or less viscous liquid.

These disposable devices contain a source of energy such as a pressurized gas generator, delivering a gas suddenly released on a plunger fitted into a cylinder formed by a glass tube, to propel the fluid contained under this piston towards an injection nozzle in contact with the skin, and inject it under this skin.

The glass tube having a collar at each end undergoes during its preparation a complete cycle carried out in a controlled air environment, comprising successively a washing, a drying, a silicone deposition, a depyrogenation and a final sterilization.

Moreover, the syringes usually used for a needle injection, comprising a plunger pushed by an operator, generally include a tube having a single-ended collar. For the preparation cycle of these tubes, they are inserted into holding circular bores formed on a tray, their collars forming flanges bearing above the bores, and holding these tubes vertically.

In this manner, a set of tubes disposed in the same tray is easily handled in different apparatuses to carry out the series of preparation operations. The handling of the tubes is made in a simple, fast and secure manner.

Nonetheless, as regards tubes, in particular glass tubes, including a collar at each end having similar diameters, this type of tray cannot be used because the circular holding bores having a diameter sufficient to receive the lower collar of the tube, could not then retain the upper collar.

SUMMARY

This section provides a general summary of the disclosure and is not a comprehensive disclosure of its full scope or all of its features.

The present disclosure provides a tray intended to hold injection device tubes including a collar at each end of a body, in order to carry out operations of preparing these tubes, this tray comprising bores each intended to receive the body of the tube, being remarkable in that each bore includes a holding portion not letting through the upper collar of the tube, which extends laterally by an introduction portion enabling the passage of the lower collar.

An advantage of this tray is that in a simple, fast and efficient manner, an operator can introduce a collar of each tube into the introduction portion, then make this tube slide laterally towards the holding portion. The tube is then held vertically by its upper collar retained above the bore.

Thus, each bore includes a holding portion configured to not let through the upper collar of the tube, said holding portion extending laterally by an introduction portion configured to enable the passage of the lower collar of the tube.

The tray for holding the tubes according to the present disclosure may further include one or more of the following features, which may be combined together.

Advantageously, each bore includes, on a front side, the holding portion having forwards a circular-arc-shaped contour intended to adjustably receive the body of the tube.

In this case, advantageously the holding portion extends rearwardly by the introduction portion including a circular-arc-shaped contour intended to enable the passage of the lower collar of the tube. In this manner, a bore with a minimum surface is obtained to preserve the rigidity of the tray, enabling both the introduction of the tube and the holding thereof.

Advantageously, the holding portion includes forwards a vertical wall. This wall increases the vertical holding of the tubes in the tray.

Advantageously, the tray includes elastic elements disposed between the holding portion and the introduction portion. These elastic elements enable a clipping of the tube in the holding portion, providing its positioning in this portion.

In particular, the elastic elements may form tabs each having a boss separating the holding portion from the introduction portion.

Advantageously, the tray includes a plastic material comprising liquid crystal polymers, implemented by injection. This plastic material has both a good rigidity, a resistance to different chemical agents and a resistance to the high temperatures of dry sterilization.

The present disclosure also relates to a method for processing tubes contained in a tray comprising any one of the preceding features, which previously coats the silicone tubes, then sterilizes the tray supporting the tubes through a dry heat process.

In addition, the present disclosure relates to a method for processing tubes contained in a tray comprising any one of the preceding features, which disposes the tray supporting the tubes in a standardized support, then in a sealed bag made of a high-density polyethylene, before a sterilization cycle.

In addition, the present disclosure relates to a method for processing tubes contained in a tray comprising any one of the preceding features, which includes a final step of conditioning the tray supporting the tubes, carried out according to the standard French norm "NF ISO 11040-7."

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
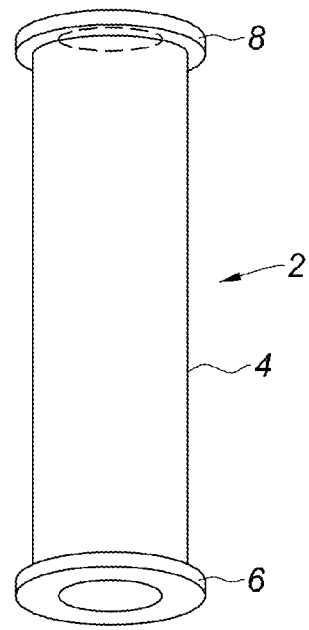
FIG. 1 shows a glass tube of a needleless injection device, including a collar on each side.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

For more clarity, identical or similar elements are marked with identical reference signs in all figures.

FIG. 1 shows an injection device glass tube 2, including a cylindrical body 4 having a lower collar 6 and an upper collar 8, each forming an external bead of revolution around the main axis of the body.

The glass tube 2 can be used in particular by the injection device presented above and illustrated by the document of the prior art FR-A1-3038232.

Figure 2:
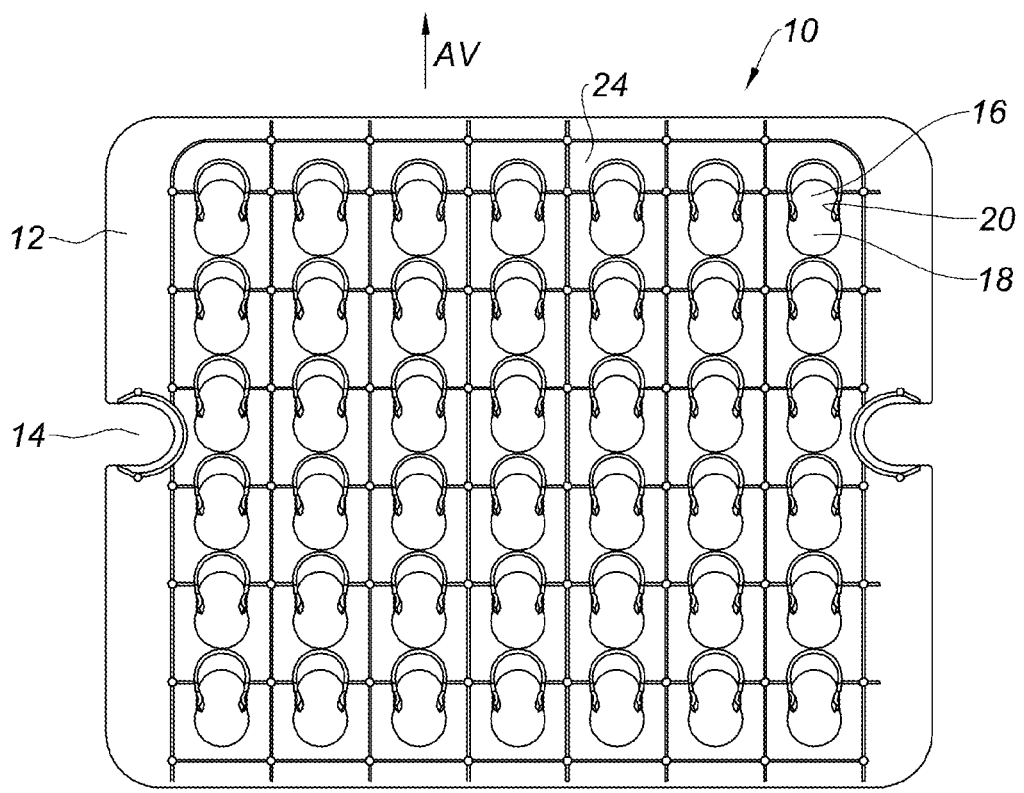
FIG. 2 shows a tray with a bore intended to receive one or more glass tubes depicted in FIG. 1 according to the present disclosure.
Figure 3:
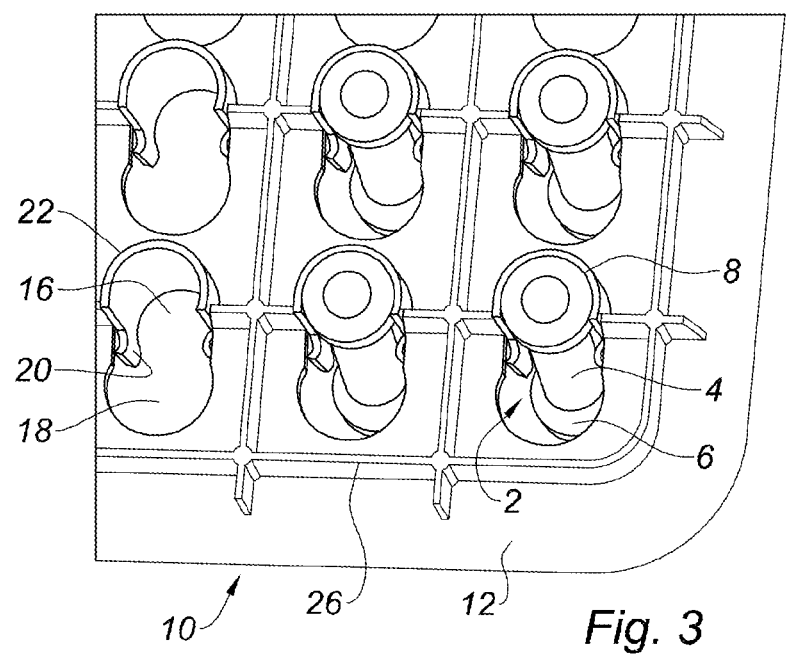
FIG. 3 is a detail view of the tray according to the present disclosure.
Figure 4:
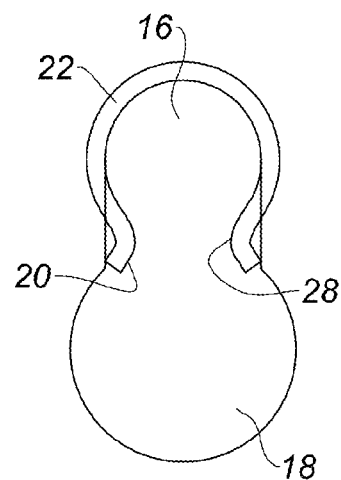
FIG. 4 is a top view of a bore of the tray according to the present disclosure.

FIGS. 2, 3 and 4 show a rectangular shaped tray 10, comprising, in a transverse direction, a side conventionally called front side, indicated by the arrow "AV."

The tray 10 includes a planar plate 24 having a flat contour 12 comprising at the middle of the two sides perpendicular to the front direction, an indentation 14 facilitating the handling of the tray.

The tray 10 includes, in the front-rear direction, seven identical rows of six bores, each of these bores being intended to receive a glass tube 2 which is held by presenting its axis perpendicular to this tray.

A network of ribs 26 surrounds the bores to stiffen the planar tray 24.

Each bore includes a front holding portion 16 having forwards a semicircular contour comprising a vertical wall 22 protruding above the tray 24, which is substantially adjusted around the body 4 of a glass tube 2.

The upper collar 8 of the glass tube 2 rests on the top of the vertical wall 22, the height of the wall is substantially equal to the diameter of the body 4, providing a vertical holding of this tube.

The front holding portion 16 of each bore extends rearwardly (opposite the AV arrow direction shown in FIG. 2) by two straight parallel sides, which open into a rear introduction portion 18 including a circular contour having a diameter slightly larger than that of the lower collar 6.

At the height of the planar tray 24, the vertical wall 22 extends rearwardly, at the level of each straight parallel side connecting the front holding portion 16 to the rear introduction portion 18, by an elastic tab 20 originating from the vertical wall. Each elastic tab 20 has a curvature which first follows the circular contour of the front holding portion 16, then after a central boss 28 turned inwardly, which follows the circular contour of the rear introduction portion 18.

The minimum distance between the two bosses 28 of the elastic tabs 20 is a little smaller than the diameter of the body 4 of the glass tube 2.

After having introduced the lower collar 6 of a glass tube 2 into the rear introduction portion 18, the tube is pressed forwardly, its body 4 fitting between the two tabs 20 to separate them by elastic deformation by pressing on their central boss 28.

After having passed the bosses of the tabs 20, the glass tube 2 is pushed by these tabs forwardly to fit to the bottom of the front holding portion 16, against the vertical wall 22.

At the end, a vertical holding of each glass tube 2 is obtained thanks to the upper collar 8 placed above the vertical wall 22, and the two tabs 20 which constantly press on the body 4 forwards to flatten it on the vertical wall.

Figure 5:
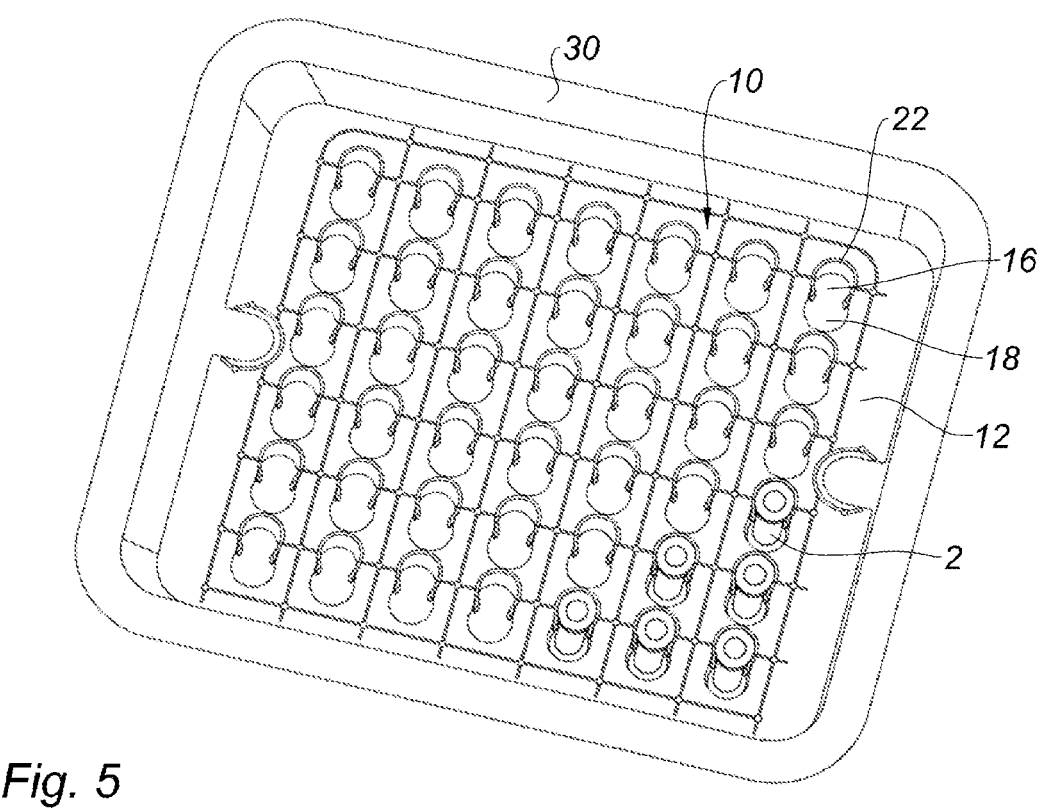
FIG. 5 is a perspective view of the tray adjusted in a contour provided for a standardized conditioning according to the present disclosure.

FIG. 5 shows the tray 10 adjusted in a standardized support 30 forming a contour, also called "Tub," enabling a positioning in different apparatuses for processing the glass tubes 2. The entire tray 10 is then bagged with its support 30, receiving a set of glass tubes 2, and a sealing of this bag to achieve a sterilization of the tubes.

Advantageously, bags made of a plastic material, using a high density polyethylene, are used which may in particular be a material marketed under the trademark "Tyvek," allowing for a reduced passage of moisture, a good heat conduction, a strong microbial barrier, and a high mechanical strength, in particular for the resistance to the perforations.

The final conditioning is advantageously carried out according to the standard French norm "NF ISO 11040-7," specifying the packaging of systems for delivering sterilized tubes ready to be filled.

Advantageously, after the washing of the tubes 2, a silicone coating is carried out, followed by a sterilization through a pyrogens reduction process comprising a dry heat heating to obtain a strong reduction of the endotoxins which are pyrogens.

In particular, a heating cycle in dry heat at 240° C. has the advantage of simultaneously achieving a crosslinking of the silicone, which subsequently avoids releases of the silicone into the drug after the filling of the glass tube 2, and during the end use of the injection device on the patient. In addition, this method avoids a sterilization with ethylene oxide which introduces toxic materials.

Advantageously, the tray 10 is made by injection molding of a plastic material comprising liquid crystal polymers, called "LCP" (Acronym standing for "Liquid Crystal Polymer"), which are materials with a high mechanical performance resistant to the dry heat cycle at 240° C., as well as to various chemical agents.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

Spatially relative terms, such as "inner," "outer," "beneath," "below," "lower," "above," "upper," "front", "rear", "rearwardly" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above or below. The device may be otherwise oriented (rotated 90 degrees or at other orientations) and the spatially relative descriptors used herein interpreted accordingly.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A tray for holding injection device tubes including a collar at each end of a body, the tray comprising bores that receive the body of the tube, wherein each bore includes a holding portion configured to hold an upper collar of the tube and an introduction portion configured to enable passage of a lower collar of the tube, wherein the holding portion extends laterally from the introduction portion within a same plane of the tray, wherein the holding portion includes a vertical wall having a height substantially equal to a diameter of the body of the tube, the tray further comprising elastic elements disposed between the holding portion and the introduction portion, wherein the elastic elements form tabs, each tab including a boss separating the holding portion from the introduction portion, wherein the height of the vertical wall is at least a minimum distance between the bosses separating the holding portion from the introduction portion.

2. The tray according to claim 1, wherein each bore includes, on a front side, the holding portion having a circular-arc-shaped contour to adjustably receive the body of the tube.

3. The tray according to claim 2, wherein the holding portion extends rearwardly from the introduction portion, the introduction portion including a circular-arc-shaped contour configured to enable the passage of the lower collar of the tube.

4. The tray according to claim 1, wherein the tray includes a plastic material comprising liquid crystal polymers, implemented by injection.

5. The tray according to claim 1, wherein the introduction portion is directly connected to the holding portion.

6. The tray according to claim 1, wherein the introduction portion and holding portion jointly define a closed shape.

7. The tray according to claim 1, wherein the height of the vertical wall is substantially equal to a diameter of the holding portion.

* * * * *